United States Patent [19]
von Gentzkow et al.

[11] Patent Number: 5,389,534
[45] Date of Patent: Feb. 14, 1995

[54] BIOSENSOR CONTAINING A BIOCHEMICAL SUBSTANCE IMMOBILIZED ON A LAYER OF AN OLEFINIC-UNSATURATED, EPOXYFUNCTIONAL POLYETHER

[75] Inventors: Wolfgang von Gentzkow, Kleinsendelbach; Hans-Dieter Feucht, Renningen, both of Germany

[73] Assignee: Siemens Aktiengesellschaft, Munich, Germany

[21] Appl. No.: 35,019

[22] Filed: Mar. 22, 1993

[30] Foreign Application Priority Data

Mar. 23, 1992 [DE] Germany ............... 4209370

[51] Int. Cl.$^6$ ............ C12N 11/08; C12N 11/06; C12M 1/40; G01N 33/545
[52] U.S. Cl. ................... 435/180; 204/403; 435/176; 435/177; 435/181; 435/288; 435/817; 436/531; 436/532; 530/815; 530/816
[58] Field of Search ............. 435/174, 180, 181, 288; 436/531, 532; 530/815, 816; 204/403

[56] References Cited

U.S. PATENT DOCUMENTS

| | | | |
|---|---|---|---|
| 3,844,892 | 10/1974 | Matthews | 435/181 |
| 3,853,708 | 12/1974 | Porath et al. | 435/181 |
| 4,268,423 | 5/1981 | Rohrbach et al. | 435/180 |
| 4,352,884 | 10/1982 | Nakashima et al. | 435/180 |
| 4,612,288 | 9/1986 | Bigwood et al. | 435/180 |
| 4,832,797 | 5/1989 | Vadgama et al. | 204/1 T |
| 5,109,089 | 4/1992 | Birkle et al. | 526/273 |

FOREIGN PATENT DOCUMENTS 0291130 11/1988 European Pat. Off. .

OTHER PUBLICATIONS

Hartmeier, W., "Immobilisierte Biokatalysatoren", Springer-Verlag Berlin, Heidelberg 1986, pp. 23–51.
Woodward, J., "Immobilised cells and enzymes", IRL Press, Oxford, Washington, D.C. (1985), pp. 3–54.
"Ber. Bunsenges. Phys. Chem.", vol. 92 (1988), pp. 1423–1426.
"Sensors and Actuators", vol. 13 (1988), pp. 165–172.
"Sensors and Actuators", vol. 18 (1989), pp. 329–336.
"Chemical Economy & Engineering Review", vol. 17 (1985), No. 7–8, pp. 22–27.
"IEEE Trans. Electron Devices", vol. Ed–36 (1989), pp. 1303–1310.
"Proc. 3rd Int. Conf. Solid State Sensors and Actuators (Transducers '85)", Jun. 11–14 (1985), pp. 148–151.

*Primary Examiner*—David M. Naff
*Attorney, Agent, or Firm*—Kenyon & Kenyon

[57] ABSTRACT

A biosensor is prepared having a selective detection system containing a biochemical substance such as an enzyme immobilized by reaction with epoxy groups of an olefinic-unsaturated, epoxyfunctional polyether. Prior to immobilization, the polyether is applied to a carrier and crosslinked by treatment with high-energy radiation or peroxide to form a layer. After reacting the biochemical substance with epoxy groups, non-reacted epoxy groups are reacted with a compound containing an amino group and/or a carboxyl group such as an amino acid. Before immobilizing of the biochemical substance and after crosslinking, the polyether may be hydrophilized by reacting some of the epoxy groups with a hydrophilic compound such as an amino acid.

12 Claims, No Drawings

BIOSENSOR CONTAINING A BIOCHEMICAL SUBSTANCE IMMOBILIZED ON A LAYER OF AN OLEFINIC-UNSATURATED, EPOXYFUNCTIONAL POLYETHER

FIELD OF THE INVENTION

The invention relates to biosensors with a selective detection system consisting of a polymer and a biochemical substance, particularly an enzyme.

BACKGROUND OF THE INVENTION

Biosensors are chemosensors with a biological detection system. This detection system consists of biologically active substances, such as enzymes, antibodies, lectins, hormone receptors, etc., which are immobilized on the surface of the sensor or in a thin layer located on it. In the detection process, a change is produced on the surface or in this layer of the sensor, by interaction with the gaseous or liquid medium to be characterized, which can be evaluated using electrical, optical, mechanical, acoustical or calorimetric measurement methods. In the case of equipment with electronic data acquisition and evaluation, the active surface or layer is directly coupled, as a signal emitter, with a signal transformer, called a transducer, which is connected with the evaluation electronics for this purpose.

The reliability of the entire sensor depends on the assignability and reproducibility of the signals generated in the sensitive layer of the biosensor. This means that the layer must demonstrate not only high selectivity and sensitivity, but also a function that is free of hysteresis and drift, as well as chemical and biological stability and contamination resistance. For technical use, in particular, ease of operation, easy integration and the lowest possible measurement/regeneration time requirement, but also great long-term stability are required, while the production of the layer—according to methods which are efficient in terms of production technology and can be automated—is supposed to be as simple, reproducible and inexpensive as possible, and such that it can be integrated into the production process for sensor production.

Until now, only such biosensors which are based on enzymatic reactions have achieved any practical importance. In these reactions, the circumstance is used that products which can easily be detected, such as $H^+$, $O_2$, $H_2O_2$, $CO_2$ and $NH_3$, are formed or consumed. With regard to selectivity and sensitivity, the enzymatic reactions fully meet the requirements. But a difficulty exists in immobilizing the enzymes—without loss of activity—in as thin a detection layer as possible, in such a way that they are easily accessible for the substances to be detected, and are resistant to poisoning as well as biochemical pollutants, and remain functionally stable for as long as possible.

For the immobilization of enzymes, the following methods have been known:
adsorption on carrier surfaces
ionic binding to carrier surfaces
covalent binding to carrier surfaces
absorption in polymer layers
inclusion in a polymer lattice (matrix sheathing, microencapsulation)
inclusion by sheathing with a membrane (macroencapsulation)
cross-linking or copolymerization with difunctional or polyfunctional monomers.

However, as is evident from the extensive literature on the immobilization of enzymes, all of these methods have disadvantages, which make them appear unattractive for industrial sensor production (see, for example: W. Hartmeier, "Immobilisierte Biokatalysatoren" ["Immobilized Biocatalysts"], Springer-Verlag Berlin, Heidelberg 1986, pages 23 to 51, as well as J. Woodward, "Immobilised cells and enzymes", IRL Press, Oxford, Washington DC, 1985, pages 3 to 54).

Thus, adsorption and ionic binding of enzymes at the surface results in relatively unstable systems with a limited range of use: Changes in the pH and the ion intensity of solutions in contact with it, or the presence of other substances, already result in displacement of the surface-bound enzyme and thus to activity losses of the detection system. Also in the case of absorption in polymer layers, with plasticized polyvinyl chloride being used in the predominant number of cases (see, for example: "Sensors and Actuators", Vol. 18 (1989), pages 329 to 336, and "Ber. Bunsenges. Phys. Chem." ["Reports of the Bunsen Society for Physical Chemistry"], Vol. 92 (1988), pages 1423 to 1426), relatively unstable systems are obtained: migration and extraction of the enzymes result in a constant decrease in activity (drift) and limit the lifetime of the sensor.

Significantly more stable systems are achieved if the enzymes are covalently bound to a carrier surface, made insoluble via cross-linking or copolymerization, or are immobilized by microencapsulation or macroencapsulation. For the formation of covalent bonds and for cross-linking, free amino, carboxyl, hydroxyl and mercapto groups are available on the part of the enzymes. Both inorganic materials, such as glass, and natural and synthetic organic polymers can be used as the carrier material. A prerequisite in this connection is that the carrier materials contain reactive groups, such as isocyanate, isothiocyanate, acid chloride and epoxy groups. Less reactive groups can be activated, for example carboxyl groups can be activated using the carbodiimide or azide method, hydroxyl groups can be activated using the bromine cyan method, and amino groups can be activated using the isothiocyanate or azo method. It was possible, particularly on the basis of acrylic acid and methacrylic acid derivatives, to produce numerous reactive copolymers with dinitrofluorophenyl, isothiocyanate, oxirane or acid anhydride groups. Polyacrylamides with oxirane groups as well as modified copolymers on the basis of vinyl acetate and divinyl ethylene urea with oxirane groups are commercially available, for example.

Immobilization by cross-linking or by copolymerization represent special forms of covalent binding. In these methods, the formation of covalent bonds takes place between the enzyme molecules and difunctional or polyfunctional monomers, such as glutardialdehyde, or, in the case of copolymerization, additionally between the enzyme molecules and a polymerizing substance. In this manner, insoluble aggregates with a high molecular weight are formed. Cross-linking is generally used as an immobilization method in combination with one of the other methods, for example in combination with adsorption or absorption. Here, the enzyme molecules are first adsorbed on the surface of the carrier, or are absorbed in a layer located on it, and subsequently cross-linked.

A significant disadvantage of immobilization by covalent binding is the great stress on the biocatalysts connected with it. The immobilization procedures that are necessary, some of which are rough, in which a strong change in the pH occurs, organic solvents have to be used or reaction with reactive substances with a low molecular weight takes place, almost always lead to strong conformation changes and thus to activity losses of enzymes bound in such manner.

In immobilization by inclusion, i.e., microencapsulation or macroencapsulation, the enzymes themselves are not made insoluble, rather their reaction range is limited by semipermeable polymers or polymer layers. A prerequisite for the ability of enzymes sheathed in this manner to function is that substrates and products can pass through the sheathing substance, while the enzymes themselves have to be held back. In addition to natural polymers, such as alginate, carrageenan, pectin, agar and gelatin, which are, however, too large-meshed for permanent immobilization of enzymes, synthetic polymers, such as polyacrylamide, are particularly used for matrix sheathing. Polyamides, polyurethanes, polyesters and polyureas, for example, are used for encapsulation. The inclusion method has the disadvantage that relatively thick layers with long sensor response times are formed.

In the methods described, immobilization of the enzymes is carried out by hand in most cases, which is relatively slow, expensive and not very reproducible, and is contrary to integration into modern production processes. In view of the advantages which enzyme sensors on an FET basis (ENFETs) would be able to offer, attempts have been made in recent years to include enzyme immobilization into the planar technology in the production of integrated circuits. Thus, for example, the production and direct photo-structuring of layers based on polyvinyl alcohol which contain enzymes and can be photo-cross-linked has been described ("Proc. 3rd Int. Conf. Solid State Sensors and Actuators (Transducers '85)", Jun. 11–14, 1985, pages 148 to 151). For the purpose stated, it is also known to use photosensitive polyvinyl pyrrolidone ("IEEE Trans. Electron Devices", Vol. ED-36 (1989), pages 1303 to 1310). According to this method, structures which exactly cover the gates of the FETs can be produced on wafers. However, this method has the great disadvantage that the enzymes are at least partially inactivated during UV irradiation.

It is also known to utilize enzyme inactivation by means of UV radiation, in that first a layer of acetyl cellulose containing an enzyme is produced, the enzyme is cross-linked with glutardialdehyde in this layer, and subsequently it is irradiated through a mask in such a way that the gate coverings are shaded and therefore remain active, while the remaining areas are inactivated ("Chemical Economy & Engineering Review", Vol. 17 (1985), No. 7–8, pages 22 to 27). The inactivated layer remains on the sensor, which proves to be a disadvantage for further insulation and packaging of the sensor required for its use.

The lift-off technique has also been described ("Sensors and Actuators", Vol. 13 (1988), pages 165 to 172). In this method, a photoresist is structured in such a way that only the gate surfaces remain free. The enzyme is then applied to this, together with glutardialdehyde, and cross-linked; the photo varnish is removed with acetone and ultrasound, using the lift-off technique. Here again, it is impossible to avoid at least partial denaturing of the enzyme.

SUMMARY OF THE INVENTION

It is an object of the invention to provide a biosensor with a selective detection system (composed of a polymer and a biochemical substance), which can be produced in technically simple, efficient and low-cost manner, where the production method is such that it can be integrated into modern production systems, and yields detection systems with stable function, if necessary also miniaturized and integrated, with uniform quality and long life expectancy, in a reproducible manner.

This is accomplished, according to the invention, by applying an olefinic-unsaturated, epoxyfunctional polyether to a carrier material in the form of a layer. The polyether is cross-linked to form a large-mesh epoxyfunctional polymer matrix by means of high-energy radiation. The layer is treated with an aqueous solution of the biochemical substance, whereby the biochemical substance is immobilized in the polymer matrix by reaction with epoxy groups. The layer is then stabilized by reaction of non-converted epoxy groups with a compound containing amino and/or carboxyl groups.

DETAILED DESCRIPTION OF THE INVENTION

The invention utilizes a new type of immobilization of enzymes and other biochemical substances with selective detection properties, specifically in layers of radiation-cross-linked epoxyfunctional polyethers. It was surprisingly found that these substances are able to penetrate into large-mesh cross-linked epoxyfunctional polyethers—from aqueous solution—and can be anchored in the polymer matrix, i.e., in the polymer network, under very mild conditions by reaction with epoxy groups in chain position. This fact is completely new, and it allows for the possibility of carrying out the production, structuring and cross-linking of the layers before immobilization of the biochemical substances, and thus of avoiding damage to the substances, most of which are very sensitive, by the processes mentioned.

The production of the detection system of the biosensor according to the invention includes the following steps, in general:

1. LAYER PREPARATION

An epoxyfunctional polyether which can be cross-linked by radiation, or a mixture of such polyethers is applied, in the desired layer thickness, to a carrier material, if necessary in combination with a cross-linking initiator, a cross-linking reinforcer and/or other additives. Depending on the application case and the carrier material, this can be done out of a solution or without solvent, by dipping, spin-coating, roller-coating, curtain-coating or another conventional process, where it might be necessary to pretreat the carrier surface with an adhesion agent The layer thickness can be controlled by adjusting the viscosity and by adding a solvent or a reactive diluent. The layer produced in this manner must be freed of volatile components, in every case, which can be done by drying or degassing, for example.

2. CROSS-LINKING OF THE LAYER

Cross-linking of the layer, i.e., the polyether, takes place by means of high-energy radiation, particularly UV, electron or γ radiation. In this connection, only the olefinic-unsaturated groups that can be polymerized by radicals are converted, while the epoxy groups are quantitatively maintained. As a result of the cross-linking, a large-mesh polymer network is formed. The layer can also be structured if projection exposure or irradiation through a mask and subsequent dissolution of the non-cross-linked regions is carried out.

3. IMMOBILIZATION OF THE BIOCHEMICAL SUBSTANCE

Upon contacting of the cross-linked layer with an aqueous solution of the biochemical substance, this substance migrates into the polymer matrix and is covalently bound there by reaction with the epoxy groups. A prerequisite for this process, along with the necessary mesh width, is sufficient hydrophilicity of the polymer network formed during cross-linking. Immobilization can therefore be accelerated by prior hydrophilization of the polyether. This is done by conversion of part of the epoxy groups with hydrophilic compounds which contain reactive groups, such as NH, OH, SH or COOH groups, causing the hydrophilic character of the polymer layer to be increased. The immobilization process can also be significantly accelerated by means of additives, such as polyvinyl pyrrolidone, which result in increased water absorption of the polyethers, as well as by solvents which are miscible with water, such as dioxane, tetrahydrofuran, alcohols or polyethers. Furthermore, several different biochemical substances can also be immobilized in a single layer, and this can be done either simultaneously or consecutively.

4. STABILIZATION OF THE LAYER

This step includes the reaction of epoxy groups remaining after immobilization, with a compound containing amino and/or carboxyl groups, particularly an amino acid. Depending on the compound used, stabilization can be utilized to achieve closer cross-linking of the layer, and thus improved mechanical strength, or for adaptation of the material properties and the material transport. Furthermore, a superficial covering of the sensor layer with one or more additional layers is possible, which might also be practical for adjusting defined diffusion conditions.

For the biosensor according to the invention, epoxyfunctional polyethers with the following structure are particularly suitable; these are the subject of copending U.S. patent application Ser. No. 08/035,016—"Polyethers", which was filed on the same day as this application:

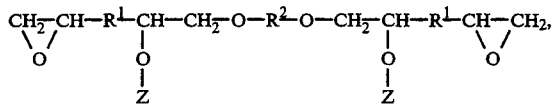

where the following applies:

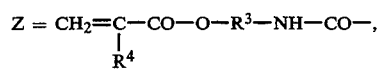

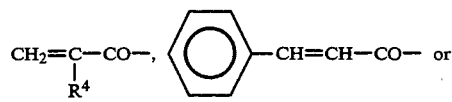

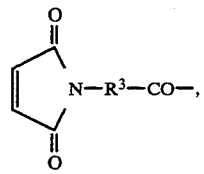

where
$R^3 = -(CH_2)_m-$, with $m = 1$ to 10
$R^4 = H$ or $CH_3$;
$R^1 = -(CH_2)_o-$, with $o = 0$ to 18, $-CH_2-O-R^5-O-CH_2-$,
where
$R^5 = -(CH_2)_p-$,

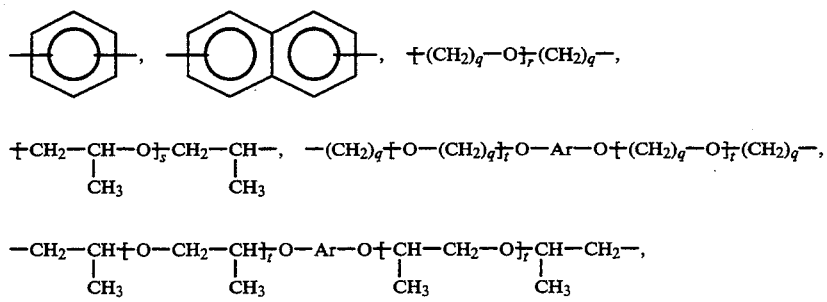

with
p=2 to 20, q=2 to 4, r=1 to 50,
s=0 to 50, t=0 to 25,
Ar=

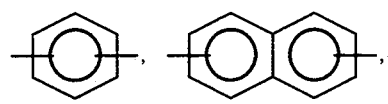

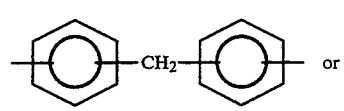

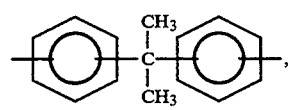

-continued $$-(CH_2)_3-\left[\begin{array}{c}CH_3\\|\\Si-O\\|\\CH_3\end{array}\right]_u\begin{array}{c}CH_3\\|\\Si-(CH_2)_3-,\\|\\CH_3\end{array}$$

with u=0 to 150, or the corresponding grouping from 3,4-epoxycyclohexylmethyl-3',4'-epoxycyclohexane carboxylate, i.e., the compound:

$$O\underset{}{\underbrace{\bigcirc}}\!\!-\!\!\underset{\underset{O}{\|}}{C}\!\!-\!\!O\!-\!\!CH_2\!\!-\!\underset{}{\underbrace{\bigcirc}}\!\!O;$$

$R^2 = -(CH_2-CH=CH-CH_2)_n-, \quad -R^6-, \quad -R^{6}-O-CO-R^7-CO-O-R^6-$ or $$-(CH_2)_3-\left[\begin{array}{c}CH_3\\|\\Si-O\\|\\CH_3\end{array}\right]_u\begin{array}{c}CH_3\\|\\Si-(CH_2)_3-,\\|\\CH_3\end{array}$$

where n=1 to 50, u=0 to 150, $R^6$ has the same meaning as $R^5$, except $$-\underset{}{\underbrace{\bigcirc}}- \text{ and } -\underset{}{\underbrace{\bigcirc\bigcirc}}-,$$

and $R^7$ has the following meaning:

$-(CH_2)_v-$, $-(CH_2)_{q-1}-O+(CH_2)_q^{-}O\}_s(CH_2)_{q-1}-$, $-(CH_2)_{q-1}+O+(CH_2)_q\}_tO-Ar-O+(CH_2)_q^{-}O\}_t(CH_2)_{q-1}-$, with q=2 to 4, s=0 to 50, t=0 to 25, v=0 to 20, and Ar has the meaning indicated above.

The polyethers according to the invention are epoxyfunctional polyether resins that can be cured with radiation; such compounds have not been known until now. These compounds demonstrate the advantageous properties of polyethers in their cured state, and, if they contain urethane groupings, also the advantageous properties of polyurethanes. Because of the presence of the epoxy groups, it is also possible to modify the cured resins and thus to vary their properties. It is advantageous if curing of the polyether resins according to the invention is carried out by irradiation, since structuring is possible in this way; in this connection, substrates in layer form are used.

The new epoxyfunctional polyethers are produced in such a manner that first, $\alpha,\omega$-diepoxides with the general formula $$CH_2\!\!-\!\!\underset{O}{\underbrace{CH}}\!\!-\!\!R^1\!\!-\!\!\underset{O}{\underbrace{CH}}\!\!-\!\!CH_2,$$

where $R^1$ has the meaning indicated above, are brought to reaction with $\alpha,\omega$-diols with the general formula $$HO-R^2-OH,$$

where $R^2$ has the meaning indicated above, in a molar ratio of 2:1, at temperatures $\leq 70°$ C., in the presence of a catalyst. This results in the formation of 2:1 adducts containing hydroxyl groups, with the following structure:

$$CH_2\!\!-\!\!\underset{O}{\underbrace{CH}}\!\!-\!\!R^1\!\!-\!\!\underset{\underset{H}{|}}{CH}\!\!-\!\!CH_2\!\!-\!\!O\!\!-\!\!R^2\!\!-\!\!O\!\!-\!\!CH_2\!\!-\!\!\underset{\underset{H}{|}}{CH}\!\!-\!\!R^1\!\!-\!\!\underset{O}{\underbrace{CH}}\!\!-\!\!CH_2.$$

To adjust the 2:1 adducts to be curable, their OH groups are reacted with cross-linking groups that can be polymerized with radicals, specifically under such reaction conditions that the epoxy groups are maintained, i.e., are not changed. When this is done, epoxyfunctional polyether resins with cross-linking groups that can be cured with radicals are formed. To introduce the cross-linking groups, the following compounds, in particular, can be used: isocyanatoalkyl (meth)acrylate, (meth)acrylic acid chloride or anhydride, cinnamic acid chloride and carboxylic acid chlorides containing maleinimide groups.

The following compounds are used as $\alpha,\omega$-diepoxides:

aliphatic diepoxides;
aliphatic, aromatic and aliphatic/aromatic diglycidyl ethers, which can contain hetero atoms, such as O, in the main chain;
cycloaliphatic diepoxides, such as 3,4-epoxycyclohexylmethyl-3',4'-epoxycyclohexane carboxylate;
silicon-organic diepoxides.

The following compounds serve as $\alpha,\omega$-diols:

$\alpha,\omega$-alkane diols;
$\alpha,\omega$-hydroxy-terminated polyethers;
$\alpha,\omega$-hydroxy-terminated polyesters;
$\alpha,\omega$-hydroxyalkyl-terminated polysiloxanes;
$\alpha,\omega$-hydroxy-terminated polybutadiene.

The reaction of the diols with the diepoxides, which is carried out in an inert solvent or in substance, generally takes place in the presence of a strong organic acid, such as trifluoromethane sulfonic acid, as the catalyst. For this purpose, however, a poly(perfluoroalkylene) sulfonic acid, for example, can also be used. During the subsequent reaction of the 2:1 adducts containing hydroxyl groups with the compound containing the group which can be cross-linked with radicals, a catalyst is also used. In the case of isocyanates, this is a Lewis acid, for example dibutyl tin dilaurate. In the case of acid anhydrides, N-methyl imidazole can serve for this purpose. In the reaction with carboxylic acid chlorides, organic bases, such as pyridine or quinoline, can be used as acid acceptor and catalyst.

The epoxyfunctional polyether resins produced in this manner, which have double bonds, can be applied according to ordinary methods, such as spin-coating, roller-coating or curtain-coating, spreading and electrostatic coating. The layer thickness can be controlled by adjusting the viscosity, if necessary by adding solvents or reactive diluents. The olefinic-unsaturated resins which contain epoxy groups can be cured with radicals, where the cured layers still have epoxy groups. The resins can be cross-linked using UV or structured, particularly after addition of a photoinitiator. The properties of the cured or structured layers, such as cross-linking density, swelling behavior and polarity, can be varied over a broad range, via the remainder $R^1$ (of the $\alpha,\omega$-epoxides) and via the remainder $R^2$ (of the $\alpha,\omega$-diols).

Modification of the resins, i.e., coupling of function carriers to the cured or structured layers, is easily possible via the epoxy groups which are present. The polyethers according to the invention can be modified in such a way that they can be used as biocompatible plastics or in membranes for biosensors and chemosensors.

The invention offers the following advantages:

Immobilization of all biochemical substances which have reactive NH, OH, SH or COOH groups at their periphery is made possible.

The layers which have the immobilized biochemical substances can also be stored dry and under non-sterile conditions, without any damage to these substances.

Immobilization of the biochemical substances takes place under very mild conditions, in aqueous solution and in the absence of reactive components with a low molecular weight; in this way losses, for example as the result of enzyme denaturing, are avoided.

A relatively small number of polymer materials with great chemical and thermal stability, which can be produced on a large technical scale and which are therefore accessible at low cost, is used for immobilization of a large number of different types of biochemical substances and for different sensor types.

The production and cross-linking of the layers, as well as their structuring, if necessary, can be carried out according to planar technology, i.e. in technically simple, reproducible and low-cost manner, and so as to be integrated into the sensor production.

Immobilization of the biochemical substances can take place independent of the layer production, depending on the need and intended use, if necessary not until just before use, to be carried out by the user.

Desorption, migration and extraction losses are avoided by chemical anchoring of the biochemical substances in the polymer matrix.

By the formation of covalent bonds between the peripheral NH, OH, SH and COOH groups of the biochemical substances and the very soft and flexible sheathing polymer material, the substances, some of which are very sensitive, for example enzymes, are given great functional and long-term stability.

Because of the possibility of the production of very thin layers ($<<1$ $\mu$m), very short sensor response times can be achieved.

Miniaturization and integration of the detection systems into microelectronic circuits, for example for the production of ISFETs and ENFETs, is without problems.

The selective detection systems are basically suitable for all sensor measurement arrangements.

The invention will now be explained in more detail in the following examples which should be regarded in an illustrative rather than a restrictive sense.

EXAMPLES 1 to 6

In a 500 ml three-neck flask (with stirrer, interior thermometer, Anschütz cap, dropping funnel and reflux condenser with drying tube), 46 mmole $\alpha,\omega$-diol (see Table 1) are placed, together with 50 g dry chloroform (stabilized with 2-methyl butene-2), and mixed with 20 drops trifluoromethane sulfonic acid. Then the apparatus is flooded with argon and the flask contents are heated to 60° C. At this temperature, 92 mmole diepoxide (see Table 1), dissolved in 100 g dry chloroform, are added within approximately 30 min, while stirring.

The reaction is continued to a residual epoxide content of 50% (see Table 1). After the end of the reaction, the heating bath is removed, then 10 g cross-linked poly-4-vinyl pyridine are added to neutralize the catalyst. Then the reaction mixture is allowed to cool down, while stirring. After 2 hours of stirring, the poly-4-vinyl pyridine is removed by pressure filtration via an 8 $\mu$m membrane filter; the reaction product remains in solution for further processing.

After balancing out the chloroform losses caused by processing, the resin solution is mixed with 20 drops dibutyl tin dilaurate solution (10 g dibutyl tin dilaurate in 100 ml chloroform) as the catalyst and with 200 mg each of hydroquinone and 2,6-di-tert.-butyl-4-methyl phenol. 14.3 g isocyanatoethyl methacrylate (92 mmole) are then dripped in within approximately 1 h, while stirring; the interior temperature is not allowed to exceed 30° C. during this time. The reaction mixture is stirred further at room temperature, until the isocyanate has completely converted, then the solvent is removed at room temperature, first in water jet pump vacuum and then in oil diffusion pump vacuum. A clear, viscous resin is obtained (see Table 1).

EXAMPLE 7

100 parts by weight of the epoxyfunctional resin which can be radiation-cured with radicals or structured, according to Example 1, are mixed with 7 parts by weight of the commercially available reactive diluent oligotriacrylate and with 2 parts by weight of the commercially available photoinitiator 2-hydroxy-2-methyl-1-phenyl propan-1-one and mixed thoroughly. A resin layer with a thickness of approximately 100 $\mu$m is poured from the mixture, and this is irradiated under nitrogen, in a commercial UV irradiation system, for 3.2 s. A clear, colorless, non-sticky cured film with an epoxide content of 90 mmole/100 g is obtained.

TABLE 1

| Example | α,ω-diol | α,ω-diepoxide | Reaction time (50% residual epoxide) | Yield | Epoxide Content mmole/100 g |
|---|---|---|---|---|---|
| 1 | 1,4-butane diol (4.1 g) | PTHF-diglycidyl ether* (80 g) | 14 h | 85 g (85%) | 92 |
| 2 | 1,6-hexane diol (5.4 g) | PTHF-diglycidyl ether* (80 g) | 14 h | 85 g (85%) | 90 |
| 3 | polytetrahydrofuran-250 (11.5 g) | PTHF-diglycidyl ether* (80 g) | 12 h | 87 g (82%) | 85 |
| 4 | THF/EO-copolyether-glycol** (57.5 g) | PTHF-diglycidyl ether* (80 g) | 15 h | 21 g (80%) | 59 |
| 5 | polytetrahydrofuran-250 (11.5 g) | 1,2,7,8-diepoxy octane (13.1 g) | 10 h | 33 g (85%) | 232 |
| 6 | 1,4-butane diol (4.1 g) | α,ω-diglycidoxypropyl polydimethyl disiloxane (87.5 g) | 15 h | 85 g (80%) | 85 |

*polytetrahydrofuran diglycidyl ether ($M_n$ = 870 g/mole)
**tetrahydrofuran/ethylene oxide copolyether glycol

EXAMPLE 8

PRODUCTION OF POLYETHER/ENZYME LAYERS 100 parts by mass of an epoxyfunctional polyether with the structure

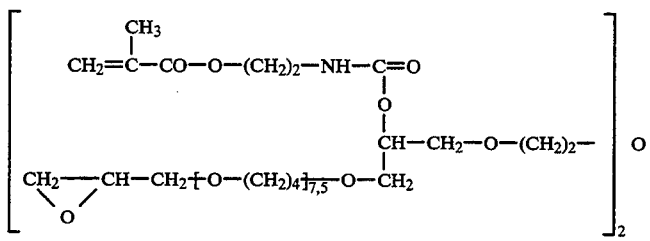

are mixed with 7 parts by mass propoxylated glycerol triacrylate as the reactive diluent and 2 parts by mass 2-hydroxy-2-methyl-1-phenyl propan-1-one as the photoinitiator, and mixed with a corresponding amount of toluene to adjust the desired processing properties. This solution is then applied to the sensitive surface of a sensor, which has been pretreated with an adhesion agent, if necessary, by dipping, dripping or spreading. Parallel to this, silicon wafers are coated with the same solution, using a varnish centrifuge; the centrifuge time is approximately 10 s.

The layers are dried in a laminar box and subsequently cross-linked under nitrogen, by UV irradiation (System F 450 of the company Fusion UV-Curing Systems) in a wavelength range of to 450 nm; irradiation period: 4.6 s. To remove soluble components, the cross-linked layers are extracted with dioxane for 24 h, at room temperature. To increase the hydrophilicity of the layers, part of the epoxy groups is reacted with compounds containing NH groups, in the form of amino acids. In this connection storage of the layers in a 2% solution of proline or glutaminic acid in a 2:1 mixture of dioxane and water at 40° to 60° C. has particularly proven to be effective. Using silicon wafers treated in a corresponding manner, the conversion can be followed by IR spectroscopy. A conversion of 50% is sufficient in most cases; if needed, however, higher values can also be adjusted.

Immobilization of the enzymes takes place by incubation of the layers in an approximately 1 to 2% solution of the enzyme in water at 20° to 30° C. To accelerate this process, the solution can be mixed with 10 to 50% dioxane, depending on the sensitivity of the enzyme. Immobilization is complete after 1 to 8 h. Remaining epoxy groups can be eliminated by gentle conversion with amino acids. As the last step, the layers are freed from extractable components by being intensively washed with water.

Table 2 contains a summary of the enzymes immobilized according to the invention, in identically pre-treated layers with a thickness of 10 μm, on silicon wafers, immobilized at 30° C. within 8 h, as well as the enzyme activity at 25° C.

TABLE 2

| Enzyme | Activity | Determination method |
|---|---|---|
| Glucose oxidase from Aspergillus niger, lyophil. 240 U/mg | 0.8 U/cm² | Gluc-DH Method of the Merck company |
| Catalase from cattle liver, suspension 65,000 U/mg | 350 U/cm² | See: B. Stellmach, "Bestimmungsmethoden Enzyme", Steinkopff-Verlag, Darmstadt 1988, pages 152 to 155 |
| Urease from broad beans, lyophil. 100 U/mg | 0.7 U/cm² | See: B. Stellmach, "Bestimmungsmethoden Enzyme", Steinkopff-Verlag, Darmstadt 1988, pages 269 to 271 |
| Alcohol dehydrogenase from yeast, lyophil. 400 U/mg | 2.0 U/cm² | See: B. Stellmach, "Bestimmungsmethoden Enzyme", Steinkopff-Verlag, Darmstadt 1988, pages 11 and 12 |
| L-asparaginase, 50% solution in glycerol 80 U/mg solution | 0.6 U/cm² | See: B. Stellmach, "Bestimmungsmethoden Enzyme", Steinkopff-Verlag, Darmstadt 1988, pages 63 to 68 |

The publication "Bestimmungsmethoden Enzyme" means "Determination Methods for Enzymes".

EXAMPLE 9

EVALUATION OF THE FUNCTIONAL STABILITY OF THE IMMOBILIZED ENZYMES

To evaluate the functional stability of enzymes immobilized according to the invention (duration: 8 h), the activities of the layers with a thickness of 10 μm, produced according to Example 8 on silicon wafers, was measured at 25° C. over a period of several weeks (see Table 2 in this regard). The activity of glucose oxidase was followed for 70 days, without any reduction in the initial value being found. Parallel to this, the activity decrease of an aqueous glucose oxidase solution was determined at 20° C., according to the determination method indicated in Table 2. This showed an activity loss of approximately 50% within 10 days, which documents the greater stability of the glucose oxidase immobilized according to the invention. An evaluation of the other immobilized enzymes listed in Table 2 yields the result that the initial activity value measured was maintained for at least 8 weeks.

EXAMPLE 10

EVALUATION OF THE FUNCTIONAL STABILITY OF BIOSENSORS WITH IMMOBILIZED ENZYMES ACCORDING TO THE INVENTION

Polyether/enzyme layers are produced on sensor measurement arrangements, according to the method described in Example 8, and their function and functional stability is followed by measurement of the resulting sensor signal. Table 3 contains the enzymes evaluated, as well as the measurement arrangement selected for the evaluation, and the useful lifetime.

TABLE 3

| Enzyme | Sensor Measurement Arrangement | Useful Lifetime |
| --- | --- | --- |
| Glucose oxidase (GOD) | oxygen sensor according to EP-OS 0 470 473 | >8 weeks |
| GOD + catalase (1:1) | oxygen sensor according to EP-OS 0 470 473 | >8 weeks |
| Urease | $NH_4^+$-sensitive glass electrode (company: Tecan AG) | >8 weeks |
| L-asparaginase | $NH_4^+$-*sensitive glass electrode* (company: Tecan AG) | >8 weeks |

What is claimed is:

1. A biosensor with a selective detection system comprising a polymer and a biochemical substance wherein the detection system is produced in the following manner:
   applying an olefinic-unsaturated, epoxyfunctional polyether to a carrier material in the form of a layer,
   cross-linking the polyether by means of high-energy radiation to form an epoxyfunctional polymer matrix,
   treating the layer with an aqueous solution of the biochemical substance, whereby the biochemical substance is immobilized in the polymer matrix by reaction with epoxy groups, and
   stabilizing the layer by reaction of non-reacted epoxy groups with a compound containing an amino group, a carboxyl group or an amino group and a carboxyl group,
wherein the polyether has the following structure:

$$CH_2\!-\!CH\!-\!R^1\!-\!CH\!-\!CH_2\!-\!O\!-\!R^2\!-\!O\!-\!CH_2\!-\!CH\!-\!R^1\!-\!CH\!-\!CH_2$$
$$\diagdown\!O\!\diagup \quad\; |\qquad\qquad\qquad\qquad\; |\qquad\quad\; \diagdown\!O\!\diagup$$
$$\qquad\qquad Z\qquad\qquad\qquad\qquad Z$$

where the following applies:

$Z = CH_2\!=\!C(R^4)\!-\!CO\!-\!O\!-\!R^3\!-\!NH\!-\!CO\!-\!$, $CH_2\!=\!C(R^4)\!-\!CO\!-\!$, $\;\;C_6H_5\!-\!CH\!=\!CH\!-\!CO\!-\!$ or a maleimide group $N\!-\!R^3\!-\!CO\!-\!$, where
$R^3 = -(CH_2)_m-$, with $m = 1$ to $10$
$R^4 = H$ or $CH_3$;
$R^1 =$ $$-(CH_2)_3\!-\!\left[\!\begin{array}{c}CH_3\\|\\Si\!-\!O\\|\\CH_3\end{array}\!\right]_u\!\!\begin{array}{c}CH_3\\|\\Si\!-\!(CH_2)_3\!-\!\\|\\CH_3\end{array}$$

with $u = 0$ to $150$,
$-(CH_2)_o-$, with $o = 0$ to $18$, or
$CH_2\!-\!O\!-\!R^5\!-\!O\!-\!CH_2-$,
where
$R^5 = -(CH_2)_p-$, phenyl, naphthyl, $+(CH_2)_q\!-\!O\!\!+_r\!(CH_2)_q\!-\!$, $+CH_2\!-\!CH(CH_3)\!-\!O\!\!+_s\!CH_2\!-\!CH(CH_3)-$, $-(CH_2)_q\!+\!O\!-\!(CH_2)_q\!+_t\!O\!-\!Ar\!-\!O\!+\!(CH_2)_q\!-\!O\!+_r\!(CH_2)_q\!-$, or $-CH_2\!-\!CH(CH_3)\!+\!O\!-\!CH_2\!-\!CH(CH_3)\!+_t\!O\!-\!Ar\!-\!O\!-$
$\qquad\qquad\qquad +CH(CH_3)\!-\!CH_2\!-\!O\!+_t\!CH(CH_3)\!-\!CH_2-$, with
$p = 2$ to $20$, $q = 2$ to $4$, $r = 1$ to $50$,
$s = 0$ to $50$, $t = 0$ to $25$,
$Ar =$

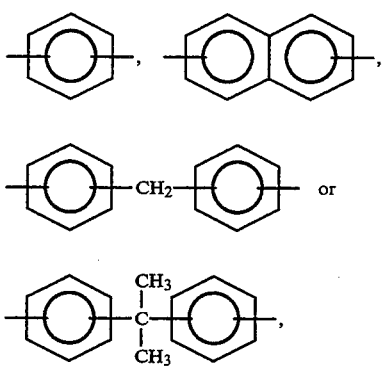

$R^2 = -(CH_2-CH=CH-CH_2)_n-$, $-R^6-$, $-R^6-O-CO-R^7-CO-O-R^6-$ or

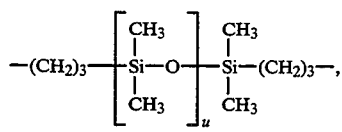

where
n=1 to 50, u=0 to 150,
$R^6$ has the same meaning as $R^5$, except that

are excluded, and
$R^7$ has the following meaning:

$-(CH_2)_v-$, $-(CH_2)_{q-1}-O-[(CH_2)_q-O]_s-(CH_2)_{q-1}-$, or $-(CH_2)_{q-1}-[O-(CH_2)_q]_t-O-Ar-O-[(CH_2)_q-O]_t-(CH_2)_{q-1}-$, with
q=2 to 4, s=0 to 50, t=0 to 25,
v=0 to 20, and
Ar has the meaning indicated above.

2. The biosensor according to claim 1 wherein the layer is structured.

3. The biosensor according to claim 1 wherein the cross-linked polyether is hydrophilized before immobilization of the biochemical substance, wherein some of the epoxy groups of the polyether are reacted with a hydrophilic compound.

4. The biosensor according to claim 1 wherein the biochemical substance is an enzyme.

5. The biosensor according to claim 1 wherein the layer is stabilized with an amino acid.

6. The biosensor according to claim 3 wherein the cross-linked polyether is hydrophilized with an amino acid.

7. A biosensor with a selective detection system comprising a polymer and a biochemical substance wherein the detection system is produced in the following manner:

applying an olefinic-unsaturated, epoxyfunctional polyether to a carrier material in the form of a layer, cross-linking the polyether by means of high-energy radiation to form an epoxyfunctional polymer matrix, treating the layer with an aqueous solution of the biochemical substance, whereby the biochemical substance is immobilized in the polymer matrix by reaction with epoxy groups, and stabilizing the layer by reaction of non-reacted epoxy groups with a compound containing an amino group, a carboxyl group or an amino group and a carboxyl group, wherein the polyether has the following structure:

$R^1-O-R^2-O-R^1$, where $R^1=$

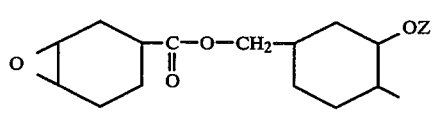

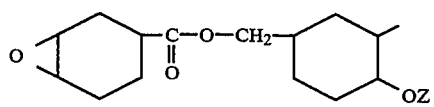

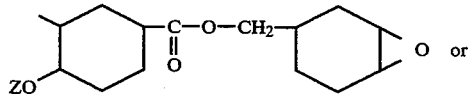

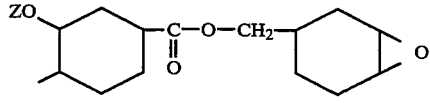

where the following applies:

$Z = CH_2=C(R^4)-CO-O-R^3-NH-CO-$,

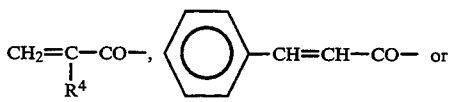

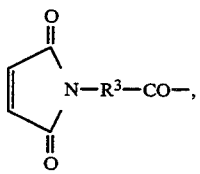

where
$R^3 = -(CH_2)_m-$, with m=1 to 10
$R^4 = H$ or $CH_3$;
$R^2 = -(CH_2-CH=CH-CH_2)_n-$, $-R^5-$,
$R^5-O-CO-R^6-CO-O-R^5-$ or

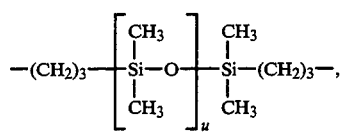

where
n=1 to 50, u=0 to 150,
$R^5$=

$-(CH_2)_p-$, $+(CH_2)_q-O+_r(CH_2)_q-$,

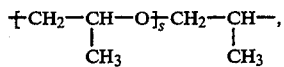

$-(CH_2)_q+O-(CH_2)_q+_rO-Ar-O+(CH_2)_q-O+_r(CH_2)_q-$, or

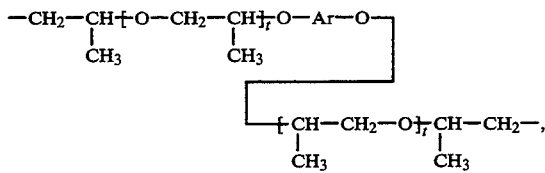

with
p=2 to 20, q=2 to 4, r=1 to 50,
s=0 to 50, t=0 to 25,
Ar=

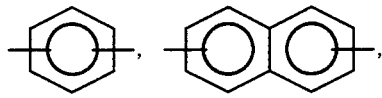

-continued

[benzene]—CH$_2$—[benzene]— or

[benzene]—C(CH$_3$)$_2$—[benzene]—, and $R^6$ has the following meaning:

$+CH_2+_v$, $+(CH_2)_{q-1}-O+(CH_2)_q+O+_s(CH_2)_{q-1}-$, or $+(CH_2)_{q-1}+O+(CH_2)_q+_rO-Ar-O+(CH_2)_q+O+_r(CH_2)_{q-1}-$, with
q=2 to 4, s=0 to 50, t=0 to 25,
v=0 to 20, and
Ar has the meaning indicated above.

8. The biosensor according to claim 7 wherein the layer is structured.

9. The biosensor according to claim 7 wherein the cross-linked polyether is hydrophilized before immobilization of the biochemical substance, wherein some of the epoxy groups of the polyether are reacted with a hydrophilic compound.

10. The biosensor according to claim 7 wherein the biochemical substance is an enzyme.

11. The biosensor according to claim 7 wherein the layer is stabilized with an amino acid.

12. The biosensor according to claim 9 wherein the cross-linked polyether is hydrophilized with an amino acid.

* * * * *